(12) United States Patent
Uhr et al.

(10) Patent No.: US 6,638,958 B2
(45) Date of Patent: Oct. 28, 2003

(54) 3-NITROISOXAZOLES AND THEIR USE IN THE PROTECTION OF MATERIALS

(75) Inventors: Hermann Uhr, Leverkusen (DE); Oliver Kretschik, Köln (DE); Martin Kugler, Leichlingen (DE); Peter Wachtler, Krefeld (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/000,499

(22) Filed: Oct. 23, 2001

(65) Prior Publication Data

US 2003/0166698 A1 Sep. 4, 2003

(30) Foreign Application Priority Data

Oct. 26, 2000 (DE) .......................................... 100 53 160

(51) Int. Cl.[7] .............................................. A61K 31/42
(52) U.S. Cl. ...................................... 514/380; 548/246
(58) Field of Search .......................... 548/246; 514/380

(56) References Cited

U.S. PATENT DOCUMENTS

| | | | |
|---|---|---|---|
| 3,207,761 A | 9/1965 | Bay | 260/307 |
| 4,845,106 A | 7/1989 | Shiokawa et al. | 514/342 |
| 5,428,032 A | 6/1995 | Shiokawa et al. | 514/226.8 |
| 5,461,167 A | 10/1995 | Shiokawa et al. | 548/202 |
| 6,022,967 A | 2/2000 | Shiokawa et al. | 548/298 |

OTHER PUBLICATIONS

Diamantini et al., 1993, Synthesis, "Nitroisoxazoles by Manganese(IV) oxide oxidation of nitro–4,5–dihydroisoxazoles", 11:1104–8.*
Bravo et al., 1966, "3–nitroisoxazoles", CA:65:2242d.*
Duranti et al., 1987, "Synthesis and in vitro antimicrobial activities of 3–nitroisoxazolic derivatives", CA:1987:420614.*
Rossi et al., Tetrahedron Letters, 1973, "A new synthesis of 3–nitroisoxazoles", 7:485–486.*
Baum et al., J. Org. Chem., 1985, "Synthesis and reactions of tetranitroethylene", 50:2736–2739.*
Duranti et al., 1987, Farmaco, Ed. Sci., 1987, "Synthesis and in vitro antimicrobial activities of 3–nitroisoxazolic derivatives", 42(4):299–306.*
J. Org. Chem. (month unavailable) 1985, 50, pp. 2736–2739, Kurt Baum and Dangjaw Tzeng, Synthesis and Reactions of Tetranitroethylene.
Tetrhedron Lett. (month unavailable) 1996, 37, pp. 7791–7794, Facile Synthesis of Nitriles from Primary Nitro Compounds Via Nitrolic Acids and Their Esters, Rae Kyu Chang and Kyongtae Kim.

Naturwissenschaften, (month unavailable) 1972, 59, p. 468, K. Eiter, Neue Synthese des Tricosen–(9–cis) („Muscalure), eines Attraktivstoffes der Hausfliege.
Tetrahedron Lett. (month unavailable) 1973, 7, pp. 485–486, S. Rossi and E. Durnati, A New Synthesis of 3–Nitroisoxazoles.
Acta Cystallogr., Sect. C. Cryst. Struct. Commun. (month unavailable) 1987, pp. 2011–2013, Don T. Cromer, Robert R. Ryan, Michael D. Coburn and P. Scheda, The Structure of 3,5–Dinitroisoxazole.
Farmaco Ed. Sc., (month unavailable) 1987, 42, pp. 299–306, E. Durnati and C. Balsamini, Sintesi Ed Attivita' Antimicrobica in Vitro Di Derivati 3–Nitroisossazolici.
Rossi, S. et al: "New synthesis of 3–nitroisoxazoles", Tetrahedron Lett. (1973), (7), 485–6, XP001055313 in der Anmeldung erwähnt Verbindungen I–VI Tabelle 1.
Chemical Abstracts, vol. 65, No. 2, 1966, Columbus, Ohio, US; abstract No. 2242d, Bravo P., et al: "3–Nitroisoxazoles" XP002190240 Verbindungen II und VI Zusammenfassung & Gazz. Chim. Ital. (1966), 96(4), 454–464.
Mechkov T.D., et al.: "Reaction of propargyl bromides with silver and sodium nitrites. New method for the synthesis of nitroisoxazoles" J. Org. Chem. USSR (Engl. Transl.) (1980), 16(6), 1148–1150, XP001055822 Seite 1148, Schema.
Diamantini, Giuseppe et al: "Nitroisoxazoles by manganese(IV) oxide oxidation of nitro–4, 5–dihydroisoxazoles" Synthesis (1993), (11), 1104–8, XP001026389 Schema 3.
Database CA Online! Chemical Abstracts Service, Columbus, Ohio, US; Duranti, Ermanno: "3–Nitroisoxazole" retrieved from STN Database accession No. 82:72851 XP002190241 3–nitroisoxazole (RN 39485–31–9); 1–(3–nitro–5–isoxazoly)–ethanone (RN 54468–91–6) Zusammenfassung & Studi Urbinati, Fac. Farm. (1972), 45(15), 65–71.
Golod E.L., et al.: "Reaction of 1,1,1,3–tetranitroalkanes with inorganic acids", J. Org. Chem. USSR (Engl. Transl.) (1973), 9(5), 1139–1143, XP001055820 Seite 1140, Schema.

* cited by examiner

Primary Examiner—Joseph K. McKane
Assistant Examiner—Robert Shiao
(74) Attorney, Agent, or Firm—Godfried R. Akorli; Diderico van Eyl

(57) ABSTRACT

The 3-nitroisoxazoles of the formula (I)

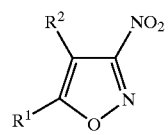

in which $R^1$ and $R^2$ are each as defined in the description, some of which are known, are highly suitable for use as biocides for protecting industrial materials.

7 Claims, No Drawings

3-NITROISOXAZOLES AND THEIR USE IN THE PROTECTION OF MATERIALS

FIELD OF THE INVENTION

The present invention relates to novel 3-nitroisoxazoles, a process for their preparation and to the use of novel and known 3-nitroisoxazoles as biocides for protecting industrial materials.

BACKGROUND OF THE INVENTION

Some 3-nitroisoxazoles having alkyl, aryl, hetaryl, alkinyl and alkoxycarbonyl radicals are known; a biological action of the compounds mentioned has not been described. (K. Baum. J. Org. Chem. 1985, 50, 2736; K. Kim, Tetrahedron Lett. 1996, 37, 7791; K. Eiter, Naturwissen-schaften 1972, 59,468; E. Duranti, Tetrahedron Lett. 1973,7, 485).

3,5-Dinitroisoxazoles are known; here, too, an antibacterial action has not been described (D. T. Corner, Acta Crystallogr., Sect. C. Cryst. Struct. Commun. 1987, 43, 2011). Specifically substituted 3-nitroisoxazole-5-carboxaldehyde derivatives are known and in some cases have weak to moderate antibacterial actions (E. Duranti II Farmaco Ed. Sc. 1987, 42, 299).

SUMMARY

The invention relates to a method comprising treating a microbe or a habitat of the microbe with a compound of the formula (I)

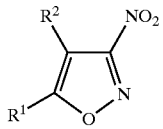

(I)

wherein $R^1$ and $R^2$ independently of one another each represent hydrogen, halogen, nitro, cyano, or represent in each case an optionally substituted alkyl, alkenyl, alkynyl or aryl, such that the compound is allowed act on the microbe or its habitat.

In one embodiment, Applicants' invention is directed to a microbicidal composition comprising: (A) a compound of the formula (I)

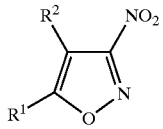

(I)

wherein $R^1$ and $R^2$ independently of one another each represent hydrogen, halogen, nitro, cyano, or represent in each case an optionally substituted alkyl, alkenyl, alkynyl or aryl, (B) solvents or diluents and, (C) optionally processing auxiliaries, or active compounds, or mixtures thereof.

In one embodiment, Applicants' invention relates to a process for preparing a compound of the formula (I)

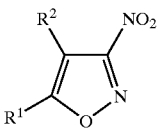

(I)

wherein $R^1$ and $R^2$ independently of one another each represent hydrogen, halogen, nitro, cyano, or represent in each case an optionally substituted alkyl, alkenyl, alkynyl or aryl, in which the process comprising reacting (i) a compound of the formula (II)

$$R^2\!-\!\!C\!\!\equiv\!\!C\!-\!R^1 \qquad (II)$$

wherein $R^1$ and $R^2$ are each as defined above with (ii) tetranitroethylene, and optionally in the presence of a diluent.

In another embodiment, Applicants' invention relates to a process for preparing a compound of the formula (I)

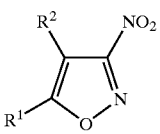

(I)

wherein $R^1$ is hydrogen, halogen, nitro, cyano, or represent in each case an optionally substituted alkyl, alkenyl, alkynyl or aryl, $R^2$ represents hydrogen. In this embodiment, the process comprises reacting (i) a compound of the general formula (III)

$$X\!-\!CH_2\!-\!C\!\!\equiv\!\!C\!-\!R^1 \qquad (III)$$

in which $R^1$ is as defined above and X represents a leaving group, preferably bromine, iodine, chlorine, tosylate or mesylate with (ii) metal nitrites, optionally, in the presence of diluents. These and other features, aspects, and advantages of the present invention will become better understood with reference to the following description and appended claims.

DESCRIPTION

It has now been found that 3-nitroisoxazoles of the general formula

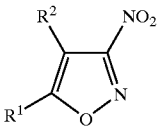

in which $R^1$ and $R^2$ independently of one another each represent hydrogen, halogen, nitro, cyano, or represent in each case optionally substituted alkyl, alkenyl, alkinyl or aryl, have excellent bactericidal action. Owing to their antibacterial and antifungal action, the compounds of the formula (I), alone or in a mixture with one another, are particularly suitable for controlling microorganisms in and on industrial materials.

Moreover, the compounds of the formula (I) have good long-term action and stability in industrial materials.

The formula (I) provides a general definition of the compounds which can be used according to the invention.

Preference is given to using compounds of the formula (I) in which $R^1$ and $R^2$ independently of one another each represent hydrogen, halogen, cyano, nitro, or represent in each case straight-chain or branched $C_1$–$C_8$-alkyl, $C_2$–$C_8$-alkenyl or $C_2$–$C_8$-alkynyl, each of which is optionally mono- or polysubstituted by identical or different substituents from the group consisting of halogen, nitro, cyano, aryl, aryloxy, $C_1$–$C_6$-alkoxy, which is optionally mono- to nonasubstituted by identical or different halogens, $C_1$–$C_6$-alkylthio, which is optionally mono- to nonasubstituted by identical or different halogens, $C_1$–$C_6$-acyl, $C_1$–$C_6$-acyloxy, $C_1$–$C_6$-alkoxy-carbonyl, amino, which is optionally mono- or disubstituted by identical or different substituents from the group consisting of $C_1$–$C_4$-alkyl and aryl, or represent $C_6$–$C_{10}$-aryl, which is optionally mono- or polysubstituted by identical or different substituents from the group consisting of halogen, cyano, nitro, $C_1$–$C_5$-alkyl, which is optionally mono- to hexasubstituted by identical or different halogens, $C_1$–$C_5$-alkoxy, which is optionally mono- to hexasubstituted by identical or different halogens, $C_1$–$C_5$-alkylthio, which is optionally mono- to hexasubstituted by identical or different halogens, amino, monoalkylamino having straight-chain or branched $C_1$–$C_6$-alkyl radicals, dialkylamino having identical or different straight-chain or branched $C_1$–$C_6$-alkyl radicals.

Particular preference is given to using compounds of the formula (I) in which $R^1$ and $R^2$ independently of one another each represent hydrogen, fluorine, chlorine, bromine, cyano, nitro, or represent in each case straight-chain or branched $C_1$–$C_6$-alkyl, $C_2$–$C_6$-alkenyl or $C_2$–$C_6$-alkynyl each of which is optionally mono- to tetrasubstituted by identical or different substituents from the group consisting of fluorine, chlorine, bromine, nitro, cyano, phenyl, naphthyl, phenyloxy, naphthyloxy, $C_1$–$C_4$-alkoxy, which is optionally mono- to heptasubstituted by identical or different substituents from the group consisting of fluorine, chlorine, bromine, $C_1$–$C_4$-alkylthio, which is optionally mono- to heptasubstituted by identical or different substituents from the group consisting of fluorine, chlorine and bromine, $C_1$–$C_4$-acyl, $C_1$–$C_4$-alkoxy-carbonyl, amino, which is optionally mono- or disubstituted by identical or different substituents from the group consisting of $C_1$–$C_4$-alkyl, phenyl and naphthyl, or represent phenyl or naphthyl, each of which is optionally mono- to tetrasubstituted by fluorine, chlorine, bromine, cyano, nitro, $C_1$–$C_4$-alkyl, which is optionally mono- to tetrasubstituted by identical or different substituents from the group consisting of fluorine, chlorine and bromine, $C_1$–$C_4$-alkoxy, which is optionally mono- to tetrasubstituted by identical or different substituents from the group consisting of fluorine, chlorine and bromine, $C_1$–$C_4$-alkylthio, which is optionally mono- to tetrasubstituted by identical or different substituents from the group consisting of fluorine, chlorine and bromine, amino, monoalkylamino having straight-chain or branched $C_1$–$C_4$-alkyl radicals or dialkylamino having identical or different straight-chain or branched $C_1$–$C_4$-alkyl radicals.

Very particular preference is given to using compounds of the formula (I) in which $R^1$ and $R^2$ independently of one another each represent hydrogen, fluorine, chlorine, bromine, cyano, nitro, methyl, ethyl, n-propyl, isopropyl, n-butyl, isobutyl, sec-butyl, tert-butyl, represent in each case all isomers of pentyl, hexyl, heptyl and octyl, allyl, vinyl, propargyl, where the alkyl radicals mentioned are in each case optionally mono- to tetrasubstituted by identical or different substituents from the group consisting of fluorine, chlorine, bromine, nitro, cyano, phenyl, phenoxy, 2,4-dichlorophenoxy, methoxy, ethoxy, n-propoxy, isopropoxy, n-butoxy, isobutoxy, sec-butoxy, tert-butoxy, trifluoromethoxy, methylthio, ethylthio, n-propylthio, isopropylthio, trifluoromethylthio, $C_1$–$C_4$-acyl, $C_1$–$C_4$-acyloxy, $C_1$–$C_4$-alkoxy-carbonyl, amino, which is optionally substituted by identical or different radicals from the group consisting of $C_1$–$C_4$-alkyl, phenyl and naphthyl, furthermore represent phenyl or naphthyl, which are in each case optionally mono- to tetrasubstituted by identical or different substituents from the group consisting of fluorine, chlorine, bromine, cyano, nitro, methyl, ethyl, n-propyl, isopropyl, trifluoromethyl, methoxy, ethoxy, n-propoxy, isopropoxy, trifluoromethoxy, methylthio, ethylthio, n-propylthio, isopropylthio, trifluoromethylthio, amino, methylamino, ethylamino, n-propylamino, isopropylamino, dimethylamino, diethylamino, methylethylamino, di-n-propylamino and di-isopropylamino.

Especially preferred is the use of compounds of the formula (I), in which $R^1$ represents hydrogen, fluorine, bromine, cyano, nitro, methyl, trifluoromethyl, difluoromethyl, methoxymethyl, ethoxymethyl, ethyl, n-propyl, isopropyl, n-butyl, isobutyl, sec-butyl, tert-butyl, n-pentyl, n-hexyl, n-heptyl, n-octyl, allyl, vinyl, propargyl, phenoxymethyl, 2,4-dichlorophenoxymethyl or phenyl, which is optionally mono- to trisubstituted by identical or different substituents from the group consisting of fluorine, chlorine, bromine, cyano, nitro, methyl, ethyl, n-propyl, isopropyl, trifluoromethyl, methoxy, ethoxy, n-propoxy, isopropoxy, trifluoromethoxy, methylthio, ethylthio, n-propylthio, isopropylthio, trifluoromethylthio, amino, methylamino, ethylamino, n-propylamino, isopropylamino, dimethylamino, diethylamino, methylethylamino, di-n-propylamino and diisopropylamino and $R^2$ represents hydrogen.

Especially preferred is furthermore the use of compounds of the formula (I) in which $R^1$ represents hydrogen, fluorine, bromine, cyano, nitro, methyl, trifluoromethyl, difluoromethyl, methoxymethyl, ethoxymethyl, ethyl, n-propyl, isopropyl, n-butyl, isobutyl, sec-butyl, tert-butyl, n-pentyl, n-hexyl, n-heptyl, n-octyl, allyl, vinyl, propargyl, phenoxymethyl, 2,4-dichlorophenoxymethyl or phenyl, which is optionally mono- to trisubstituted by identical or different substituents from the group consisting of fluorine, chlorine, bromine, cyano, nitro, methyl, ethyl, n-propyl, isopropyl, trifluoromethyl, methoxy, ethoxy, n-propoxy, isopropoxy, trifluoromethoxy, methylthio, ethylthio, n-propylthio, isopropylthio, trifluoromethylthio, amino, methylamino, ethylamino, n-propylamino, isopropylamino, dimethylamino, diethylamino, methylethylamino, di-n-propylamino and diisopropylamino, and $R^2$ represents hydrogen, fluorine, bromine, cyano, nitro, methyl, trifluoromethyl, difluoromethyl, methoxymethyl, ethoxymethyl, ethyl, n-propyl, isopropyl, n-butyl, isobutyl, sec-butyl, tert-butyl, n-pentyl, n-hexyl, n-heptyl, n-octyl, allyl, vinyl, propargyl, phenoxymethyl or phenyl.

The radicals given in the respective definitions or the preferred and particularly preferred definitions can, independently of the combination given in each case, also be replaced by any radical definitions of other combinations. Moreover, radical definitions from any preferred range may not apply.

The optionally substituted aryl radicals mentioned in the definition of $R^1$ and $R^2$ represent in particular in each case optionally substituted phenyl and naphthyl radicals.

The term halogen is to be understood as meaning in particular fluorine, chlorine and bromine.

The compounds of the formula (I) are novel and also form part of the subject-matter of the present invention, except for the compounds methyl 3-nitro-isoxazole-5-carboxylate (CAS-RN: 40995-06-0)

ethyl 3-nitro-isoxazole-5-carboxylate (Beilstein RN: 6598833)

3-nitro-5-phenylisoxazole (CAS-RN: 6455-30-7)

3-nitro-5-methylisoxazole (CAS-RN: 750097-82-2)

3-(3-nitro-isoxazol-5-yl)-prop-2-yn-1-ol (Beilstein RN: 1106231)

3,5-dinitro-isoxazole (CAS-RN: 42216-62-6)

4-methyl-3,5-dinitro-isoxazole (CAS-RN: 42216-63-7)

3-nitro-5-(3-nitro-prop-1-ynyl)-isoxazole (Beilstein RN: 1119643)

3-nitroisoxazole (CAS-RN: 39485-31-9)

4-chloromethyl-3-nitro-isoxazole (Beilstein RN: 6594348)

4-methyl-3-nitro-isoxazole (Beilstein RN: 6593345)

5-butyl-3-nitro-isoxazole (CAS-RN: 40995-04-8)

3-nitro-5-hydroxymethyl-isoxazole (CAS-RN: 75079-83-3)

5-(brom-prop-1-ynyl)-3-nitro-isoxazole (CAS-RN: 40995-02-6)

3-nitro-1-phenyl-isoxazole (Beilstein RN: 6596756)

(3-nitro-isoxazol-4-yl)-phenyl-methanone (Beilstein RN: 6599593)

4-(4-methoxy-phenyl)-3-nitro-isoxazole (Beilstein RN: 6600205)

3-nitro4-(2-nitro-phenyl)-isoxazole (Beilstein RN: 6604179)

3-nitro-4-(4-nitrophenyl)-isoxazole (Beilstein RN: 6604546)

3-nitro-4-(2,4-dinitrophenyl)-isoxazole (Beilstein RN: 6612177)

3-nitro-isoxazole-5-carbaldehyde (CAS-RN: 108802-81-9)

3-nitro-5-acetyl-isoxazole (CAS-RN: 54468-91-6).

The novel and known 3-nitroisoxazoles of the formula (I) which can be used according to the invention are obtained when compounds of the formula (II)

  (II)

in which $R^1$ and $R^2$ are each as defined above are reacted with tetranitroethylene, if appropriate in the presence of diluents (see also K. Baum, J. Org. Chem. 1985, 50, 2736).

Suitable diluents which may be used, if appropriate, are all organic solvents. These preferably include hydrocarbons, such as toluene, xylene or hexane, chlorinated hydrocarbons, such as chlorobenzene, methylene chloride or chloroform, ketones, such as acetone, ethers, such as tetrahydrofuran, diethyl ether, methyl tert-butyl ether and dioxane, nitriles, such as acetonitrile, and also DMSO, DMF and NMP.

The reaction temperatures in this process can be varied within a relatively wide temperature range. In general, the process is carried out at temperatures between −30° C. and +150° C., preferably between −10° C. and +50° C.

Tetranitroethylene can be prepared in a known manner from hexanitroethane.

The compounds of the formula (II) used are known or can be prepared by generally known processes.

Nitroisoxazoles of the general formula (I) in which $R^1$ is as defined above and $R^2$ represents hydrogen can alternatively can also be prepared by reacting compounds of the general formula (III)

  (III)

in which $R^1$ is as defined above and

X represents a leaving group, preferably bromine, iodine, chlorine, tosylate or mesylate, with metal nitrites, preferably sodium nitrite or potassium nitrite, if appropriate in the presence of diluents.

The reaction temperatures in this process can be varied within a relatively wide temperature range. In general, the process is carried out at temperatures between −30° C. and +150° C., preferably between −1° C. and +80° C.

Suitable diluents which may be used, if appropriate, are both water and all organic solvents. These preferably include hydrocarbons, such as toluene, xylene or hexane, chlorinated hydrocarbons, such as chlorobenzene, methylene chloride or chloroform, ketones, such as acetone, ethers, such as tetrahydrofuran, diethyl ether, methyl tert-butyl ether and dioxane, nitriles, such as acetonitrile, and also DMSO, DMF and NMP.

This process is suitable both for preparing the known compounds of the formula (I) and the novel compounds of the formula (I) according to the invention, where the radical $R^1$ is as defined.

The substances of the formula (I) which can be used according to the invention have potent microbicidal action and can be used for controlling undesirable microorganisms, such as fungi and bacteria, in crop protection and in the protection of materials.

In the protection of materials, the substances according to the invention can be used for protecting industrial materials against attack and destruction by undesirable microorganisms. In the present context, industrial materials are to be understood as meaning non-live materials which have been prepared for use in industry. For example, industrial materials which are intended to be protected by active compounds according to the invention from microbial change or destruction can be glues, sizes, paper and board, textiles, leather, wood, paints and synthetic articles, cooling lubricants and other materials which can be attacked or destroyed by microorganisms. Parts of production plants, for example cooling-water circuits, which may be impaired by the multiplication of microorganisms may also be mentioned in the context of the materials to be protected. Industrial materials which may preferably be mentioned in the context of the present invention are glues, sizes, paper and boards, leather, wood, paints, cooling lubricants and heat transfer liquids.

Examples of microorganisms which are capable of bringing about degradation of, or change in, the industrial materials and which may be mentioned are bacteria, fungi, yeasts, algae and slime organisms. The active compounds according to the invention preferably act against fungi, in particular molds, wood-discoloring and wood-destroying fungi (Basiidiomycetes) and also against slime organisms and bacteria.

Microorganisms of the following genera may be mentioned by way of example:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

The active compounds according to the invention, as such or in their formulations, can also be used in a mixture with known fungicides, bactericides, acaricides, nematicides or insecticides, for example to widen the activity spectrum or to prevent the development of resistance. In many cases, synergistic effects are obtained, i.e. the activity of the mixture is greater than the activity of the individual components.

The following co-components are found to be particularly favorable:
triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazol, penconazole, propioconazole, (+)-cis-1-(4-chlorophenyl)-2-(1H-1,2,4-triazol-1-yl)-cycloheptanol, 2-(1-tert-butyl)-1-(2-chlorophenyl-3-(1,2,4-triazol-1-yl)-propan-2-ol, tebuconazole, tetraconazole, triadimefon, triadimenol, triapenthenol, triflumizole, triticonazole, uniconazole and their metal salts and acid adducts;
imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;
pyridines and pyrimidines such as:
ancymidol, buthiobate, fenarimol, mepanipyrin, nuarimol, pyvoxyfur, triamirol succinate dehydrogenase inhibitors such as:
benodanil, carboxim, carboxim sulphoxide, cyclafluramid, fenfuram, flutanil, furcarbanil, furmecyclox, mebenil, mepronil, methfuroxam, metsulfovax, pyrocarbolid, oxycarboxin, shirlan, Seedvax;
naphthalene derivatives such as:
terbinafine, naftifine, butenafine, 3-chloro-7-(2-aza-2, 7,7-trimethyl-oct-3-en-5-ine);
sulfenamides such as:
dichlofluanid, tolylfluanid, folpet, fluorofolpet, captan, captofol;
Benzimidazoles such as:
carbendazim, benomyl, fuberidazole, thiabendazole or their salts;
morpholine derivatives such as:
aldimorph, dimethomorph, dodemorph, falimorph, fenpropidin fenpropimorph,-tridemorph, trimorphamid and their arylsulphonate salts such as, for example, p-toluenesulphonic acid and p-dodecylphenyl-sulphonic acid;
benzothiazoles such as:
2-mercaptobenzothiazole;
benzothiophene dioxides such as:
N-cyclohexyl-benzo[b]thiophene-S,S-dioxide carboxamide;
benzamides such as:
2,6-dichloro-N-(4-trifluoromethylbenzyl)-benzamide, tecloftalam;
boron compounds such as:
boric acid, boric ester, borax;
formaldehyde and formaldehyde-releasing compounds such as:
benzyl alcohol mono-(poly)-hemiformal, n-butanol hemiformal, dazomet, ethylene glycol hemiformal, hexa-hydro-S-triazine, hexamethylenetetramine, N-hydroxymethyl-N'-methylthiourea, N-methylolchloroacetamide, oxazolidine, paraformaldehyde, taurolin, tetrahydro-1,3-oxazine, N-(2-hydroxypropyl)-amine-methanol;
isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octyl-isothiazolin-3-one, 4,5-trimethylene-isothiazolinone, 4,5-benzoisothiazolinone;
aldehydes such as:
cinnamaldehyde, formaldehyde, glutardialdehyde, β-bromocinnamaldehyde;
thiocyanates such as:
thiocyanatomethylthiobenzothiazole, methylenebisthiocyanate;
quaternary ammonium compounds such as:
benzalkonium chloride, benzyldimethyltetradecylammonium chloride, benzyldimethyldodecylammonium chloride, dichlorobenzyl-dimethyl-alkyl-ammonium chloride, didecyidimethylammonium chloride, dioctyl-dimethyl-ammonium chloride, N-hexadecyl-trimethyl-ammonium chloride, 1-hexadecyl-pyridinium chloride, iminoctadine tris (albesilate);
iodine derivatives such as:
diiodomethyl p-tolyl sulphone, 3-iodo-2-propinyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl-cyclohexylcarbamate, 3-iodo-2-propinyl phenylcarbamate;

phenols such as:
tribromophenol, tetrachlorophenol, 3-methyl4-chlorophenol, 3,5-dimethyl-4-chlorophenol, phenoxyethanol, dichlorophene, 2-benzyl-4-chlorophenol, 5-chloro-2-(2,4-dichlorophenoxy)-phenol, hexachlorophene, p-hydroxybenzoate, o-phenylphenol, m-phenylphenol, p-phenylphenol and their alkali metal salts and alkaline earth metal salts;

microbicides with an activated halogen group such as:
bronidox, 2-bromo-2-nitro-1,3-propanediol, 2-bromo-4'-hydroxy-acetophenone, 1-bromo-3-chloro-4,4,5,5-tetramethyl-2-imidazolidinone, β-brom-β-nitrostyrene, chloracetamid, chloramin T, 1,3-dibromo-4,4,5,5-tetramethyl-2-imidazoli-dinone, dichloramin T, 3,4-dichloro-(3H)-1,2-dithiol-3-one, 2,2-dibromo-3-nitrile-propionamide, 1,2-dibromo-2,4-dicyanobutane, halane, halazone, mucochloric acid, phenyl (2-chlorocyano-vinyl) sulphone, phenyl (1,2-dichloro-2-cyanovinyl) sulphone, trichloroisocyanuric acid;

pyridines such as:
1-hydroxy-2-pyridinethione (and their Na, Fe, Mn, Zn salts), tetrachloro-4-methylsulphonylpyridine, pyrimethanol, mepanipyrim, dipyrithion, 1-hydroxy4-methyl-6-(2,4,4-trimethylpentyl)-2(1H)-pyridine;

methoxyacrylates or similar such as:
azoxystrobin, methyl (E)-methoximino[alpha-(o-tolyloxy)-o-tolyl]acetate, (E)-2-methoxyimino-N-methyl-2-(2-phenoxyphenyl)acetamide, (E)-2-{2-[6-(2-cyanophenoxy)pyrimidin-4-yloxy]phenyl}-3-methoxyacrylate, O-methyl2-[([3-methoximino-2-butyl)imino]oxy)o-tolyl]-2-methoximino-acetimidate, 2-[[[[1-(2,5-dimethylphenyl)ethylidene]amino]oxy]methyl]-alpha-(methoximino)-N-methylbenzeneacetamide, alpha-(methoxyimino)-N-methyl-2-[[[[1-[3-(trifluoromethyl)phenyl]ethylidene]amino]oxy]methyl]-benzeneacetamide, trifluoxystrobin, alpha-(methoxymethylene-2-[[[[1-[3-(trifluoromethyl)phenyl]ethylidene]amino]oxy]methyl]-benzeneacetic acid methyl ester, 2-[[[5-chloro-3-(trifluoromethyl)-2-pyridinyl]oxy]methyl]-alpha-(methoxyimino)-N-methylbenzeneacetamide, 2-[[[cyclopropyl[(4-ethoxyphenyl)imino]methyl]thio]methyl]-alpha-(methoxyimino)-benzeneacetic acid methyl ester, alpha-(methoxyimino)-N-methyl-2-(4-methyl-5-phenyl-2,7-dioxa-3,6-diazaocta-3,5-dien-1-yl)-benzeneacetamide, alpha-(methoxymethylene)-2-(4-methyl-5-phenyl-2,7-dioxa-3,6-diazaocta-3,5-dien-1-yl)-benzeneacetic acid methyl ester, alpha-(methoxyimino)-N-methyl-2-[[[1-[3-(trifluoromethyl)phenyl]ethoxy]-imino]methyl]-benzeneacetamide, 2-[[(3,5-dichloro-2-pyridinyl)oxy]methyl]-alpha-(methoxyimino)-N-methyl-benzeneacetamide, 2-[4,5-dimethyl-9-(4-morpholinyl)-2,7-dioxa-3,6-diazanona-3,5-dien-1-yl]-alpha-(methoxy-methylene)-benzeneacetic acid methyl ester, kresoxim-methyl; metal soaps such as: tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as: copper hydroxycarbonate, sodium dichromate, potassium dichromate, potassium chromate, copper sulphate, copper chloride, copper borate, zinc fluorosilicate, copper fluorosilicate;

oxides such as: tributyltin oxide, $Cu_2O$, CuO, ZnO;

dithiocarbamates such as: cufraneb, ferban, potassium N-hydroxymethyl-N'-methyl-dithiobarbamate, sodium dimethyidithiocarbamate, potassium dimethyldithiocarbamate, macozeb, maneb, metam, metiram, thiram, zineb, ziram;

nitriles such as:
2,4,5,6-tetrachloroisophthalonitrile, disodium cyano-dithioimido-carbamate;

quinolines such as:
8-hydroxyquinoline and their copper salts;

other fungicides and bactericides such as:
5-hydroxy-2(5H)-furanone, 4,5-benzodithiazolinone, 4,5-trimethylenedithiazolinone, N-(2-p-chlorobenzoylethyl)-hexaminium chloride, 2-oxo-2-(4-hydroxy-phenyl)acetohydroxycinnamoyl chloride, tris-N-(cyclohexyldiazeniumdioxy)-aluminium, N-(cyclo-hexyldiazeniumdioxy)-tributyltin or its potassium salts, bis-N-(cyclohexyldiazeniumdioxyycopper; iprovalicarb, fenhexamid, spiroxamine, carpropamid, diflumetorin, quinoxyfen, famoxadone, polyoxorim, acibenzolar S-methyl, furametpyr, trifluzamide, methalaxy-M, Ag-, Zn- or Cu-containing zeolites alone or incorporated into polymeric materials.

Very especially preferred are mixtures of compounds of the formula (I) with one or more of the following active compounds:

azaconazole, bromuconazole, cyproconazole, dichlobutrazol, diniconazole, hexaconazole, metaconazole, penconazole, propiconazole, tebuconazole, dichlofluanid, tolylfluanid, fluorfolpet, methfuroxam, carboxin, benzo[b]thiophene S,S-dioxide N-cyclohexylcarboxamide, fenpiclonil, 4-(2,2-difluoro-1,3-benzodioxol-4-yl)-1H-pyrrole-3-carbonitrile, butenafine, imazalil, N-methyl-isothiazolin-3-one, 5-chloro-N-methylisothiazolin-3-one, N-octylisothiazolin-3-one, dichloro-N-octylisothiazolinone, mercaptobenthiazole, thiocyanatomethylthiobenzothiazole, benzoisothiazolinone, N-(2-hydroxypropyl)-aminomethanol, benzyl alcohol (hemiyformal, N-methylolchloroacetamide, N-(2-hydroxypropyl)-amine-methanol, glutaraldehyde, omadine, dimethyl dicarbonate, 2-bromo-2-nitro-1,3-propanediol and/or 3-iodo-2-propinyl n-butylcarbamate.

Apart from with the abovementioned fungicides and bactericides, mixtures with a good efficacy are, moreover, also prepared with other active compounds:

insecticides/acaricides/nematicides such as:
abamectin, acephate, acetamiprid, acrinathrin, alanycarb, aldicarb, aldoxycarb, aldrin, allethrin, alpha-cypermethrin, amitraz, avermectin, AZ 60541, azadirachtin, azinphos A, azinphos M, azocyclotin, Bacillus thuringiensis, barthrin, 4-bromo-2(4-chlorophenyl)-1-(ethoxymethyl)-5-(trifluoromethy)-1H-pyrrole-3-carbonitrile, bendiocarb, benfuracarb, bensultap, betacyfluthrin, bifenthrin, bioresmethrin, bioallethrin, bromophos A, bromophos M, bufencarb, buprofezin, butathiophos, butocarboxim, butoxycarboxim, cadusafos, carbaryl, carbofuran, carbophenothion, carbosulfan, cartap, quinomethionate, cloethocarb, chlordane, chlorethoxyfos, chlorfenapyr, chlorfenvinphos, chlorfluazuron, chlormephos, N-[(6-chloro-3-pyridinylmethyl]-N'-cyano-N-methyl-ethaneimidamide, chlorpicrin, chlorpyrifos A, chlorpyrifos M, cis-resmethrin, clocythrin, cypophenothrin clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)-hydrazine, DNOC, dichlofenthion, dichlorvos, dicliphos, dicrotophos, difethialone, diflubenzuron, dimethoate, dimethyl-(phenyl)-silyl-methyl 3-phenoxybenzyl ether, dimethyl-(4-ethoxyphenyl)-silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximat, fensulfothion, fenthion, fenvalerate, fipronil, fluazuron, flucycloxuron, flucythrinate, flufenoxuron, flupyrazotos, flufenzine, flumethrin, flufenprox, fluvalinate, fonophos, formethanate, formothion, fosmethilan fosthiazate, fubfenprox, furathiocarb, halofenocid, HCH, heptenophos, hexaflumuron, hexythiazox, hydramethyinon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, lama-cyhalothrin, lufenuron, kadedrin lambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NC 184, NI 125, nicotine, nitenpyram, omethoate, oxamyl, oxydemethon M, oxydeprofos, parathion A, parathion M, penfluron, permethrin, 2-(4-phenoxyphenoxy)-ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen, pyrithiobac-sodium, quinalphos, resmethrin, RH-7988, rotenone, salithion, sebufos, silafluofen, spinosad, sulfotep, suiprofos, tau-fluvalinate, taroils, tebufenozide, tebufenpyrad, tebupirimphos, teflubenzuron, tefluthrin, temephos, terbam, terbufos, tetrachlorvinphos, tetramethrin, Tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, trichlorfon, triflumuron, trimethacarb, vamidothion, XMC, xylylcarb, zetamethrin;

molluscicides such as:
fentin acetate, metaldehyde, methiocarb. miclosamide;

Herbicides and other algicides such as acetochlor, acifluorfen, aclonifen, acrolein, alachlor, alloxydim, ametryn, amidosulfuron, amitrole, ammonium sulphamate, anilofos, asulam, atrazine, azafenidin, aziptrotryne, azimsulfuron, benazolin, benfluralin, benfuresate, bensulfuron, bensulphide, bentazone, benzofencap, benzthiazuron, bifenox, bispyribac, bispyribac-sodium, bispyribac-methyl, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlomitrofen, chloroacetic acid, chloransulam-methyl, cinidon-ethyl, chlorotoluron, chloroxuron, chlorpropham, chlorsulfuron, chlorthal, chlorthiamid, cinmethylin, cinofulsuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, flurochloridone, fluroxypyr, fomesafen, fosamine, fosametine, flamprop-isopropyl, flamprop-isopropyl-L, flumiclorac-pentyl, flumipropyn, flumioxzim, flurtamone, flumioxzim, flupyrsulfuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic, lactofen, lenacil, linuron, MCPA, MCPA-thioethyl, MCPB, mecoprop, mecoprop-P, mefenacet, mefluidide, metam, metamitron, metazachlor, methabenzthiazuron, methazole, methoropytryne, methyidymron, methyl isothiocyanate, metobromuron, metoxuron, metribuzin, metsulfuron, molinate, manolide, monolinuron, MSMA, metolachlor, metosulam, metobenzuron, naproanilide, napropamide, naptalam, neburon, nicosulfuron, norflurazon, sodium chlorate, oxadiazon, oxyfluorfen, oxysulfuron, orbencarb, oryzalin, oxadiargyl, propyzamide, prosulfocarb, pyrazolate, pyrazolsulfuron, pyrazoxyfen, pyribenzoxium, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, prometryn, propachlor, propanil, propaquizafob, propazine, propham, proisochlor, pyriminobac-methyl, pelargonic acid, pyrithiobac, pyraflufen-ethyl, quinmerac, quinocloamine, quizalofop, quizalofop-P, quinchlorac, rimsulfuron sethoxydim, sifuron, simazine, simetryn, sulfosulfuron, sulfometuron, sulfentrazone, sulcotrione, sulfosate, tar oils, TCA, tebutam, tebuthiuron, terbacil, terbumeton, terbuthylazine, terbutryn, thiazafluoron, thifensulfuron, thiobencarb, thiocarbazil, tralkoxydim, tri-allate, triasulfuron, tribenuron, triclopyr, tridiphane, trietazine, trifluoralin, tycor, thdiazimin, thiazopyr, triflusulfuron, vernolate.

Depending on their physical properties and/or chemical properties, the active compounds of the formula (I) can be converted into customary formulations, such as solutions, emulsions, suspensions, powders, foams, pastes, granules, aerosols and microencapsulations in polymeric substances.

The formulations or compositions are prepared in a manner known per se, for example by mixing the active compounds with extenders, i.e. liquid solvents or other carriers, using, if appropriate, surfactants, i.e. emulsifiers and/or dispersants and/or foam-formers. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkyl sulphonates, alkyl sulphates, aryl sulphonates, and also protein hydrolysates; suitable dispersants are: for example lignosulphite waste liquors and methyl cellulose. Tackifiers, such as carboxymethyl cellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral oils and vegetable oils.

The compositions used for protecting industrial materials generally comprise the active compounds in an amount of from 1 to 95%, preferably from 10 to 75%.

The use concentrations of the active compounds according to the invention depend on the type and the occurrence of the microorganisms to be controlled, and on the composition of the material to be protected. The optimal rate can be determined by test series. In general, the use concentrations are in the range from 0.001 to 5% by weight, preferably from 0.05 to 1.0% by weight, based on the material to be protected.

The invention is further described in the following illustrative examples in which all parts and percentages are by weight unless otherwise indicated.

PREPARATION EXAMPLES

Example 1

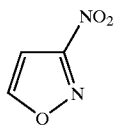

20.7 g (0.3 mol) of sodium nitrite were initially charged in 100 ml of DMF and, with cooling, treated dropwise with 22.3 g (0.15 mol) of an 80% strength solution of propargyl bromide. The color of the reaction solution changed to dark violet. The mixture was stirred at room temperature for 24 h and then poured into 300 ml of water and extracted twice with ether, and the extract was washed with saturated NaCl solution, dried over sodium sulfate and concentrated. The brown residue was chromatographed on silica gel (toluene). This gave 1.66 g of 3-nitroisoxazole as a pale yellow oil having the physical data given in Table 1.

The compounds listed in Table 1 were prepared similarly to Example 1 and the processes mentioned in the description.

TABLE 1

Compounds of the general formula (I)

| Example | $R^1$ | $R^2$ | Physical data |
|---|---|---|---|
| 1 | H | H | $^1$H-NMR (CDCl$_3$) δ = 6.99(d, 1H), 8.66(d, 1H) |
| 2 | —C$_6$H$_5$ | H | Mp = 98–102° C. |
| 3 | —CH$_3$ | H | $^1$H-NMR (CDCl$_3$) δ = 2.6(s, 3H), 6.6(s, 1H) |
| 4 | —C$_4$H$_9$ | H | $^1$H-NMR (CDCl$_3$) δ = 0.95(t, 3H), 1.42(m, 2H), 1.74(m, 2H), 2.85(t, 2H), 6.60(s, 1H) |
| 5 | (3-chloro-4-ethoxyphenyl) | H | Mp = 88° C. |
| 6 | —C$_7$H$_{15}$ | H | $^1$H-NMR (CDCl$_3$) δ = 0.9(t, 3H), 1.2–1.4(m, 8H), 1.75(m, 2H), 2.85(t, 2H), 6.5(s, 1H) |
| 7 | —CH$_2$OH | H | $^1$H-NMR (CDCl$_3$) δ = 2.4(s, 1H), 4.9(d, 2H), 6.9(s, 1H) |

Use Example A

To demonstrate the activity against bacteria, the minimum inhibitory concentrations (MIC) of the agents according to the invention are determined:

A defined Landy agar is admixed with active compounds according to the invention in concentrations of from 0.1 mg/ml to 5000 mg/ml. After the agar has solidified, it is inoculated with pure cultures of the test organisms listed in Table 2. The MIC is determined after 3 days of storage at 8° C. and 60–70% relative atmospheric humidity. The MIC is the lowest concentration of active compound at which there is no colonization by the microbial species used, it is stated in the table below.

TABLE 2

Minimum inhibitory concentration (ppm) of compounds of the formula (I) according to the invention

| Example No. | Pseudomonas aeruginosa | Bacillus subtilis |
|---|---|---|
| 1 | 100 | <40 |
| 2 | >400 | <40 |
| 3 | 200 | <40 |
| 4 | 200 | <40 |

TABLE 2-continued

Minimum inhibitory concentration (ppm) of compounds of the formula (I) according to the invention

| Example No. | Pseudomonas aeroginosa | Bacillus subtilis |
|---|---|---|
| 5 | >400 | <40 |
| 8 | 100 | <40 |

Use Example B

To demonstrate the activity against fungi, the minimum inhibitory concentrations (MIC) of the agents according to the invention are determined:

An agar which has been prepared using malt extract is admixed with active compounds according to the invention in concentrations of from 0.1 mg/ml to 5000 mg/ml. After the agar has solidified, it is inoculated with pure cultures of the test organisms listed in Table 3. The MIC is determined after 2 weeks of storage at 28° C. and 60–70% relative atmospheric humidity. The MIC is the lowest concentration of active compound at which there is no colonization by the microbial species used, it is stated in Table 3 below.

TABLE 3

Minimum inhibitory concentration (ppm) of compounds of the formula (I) according to the invention

| Example No. | Penicillium brevicaule | Chaetomium globusum | Aspergillus niger |
|---|---|---|---|
| 1 | 100 | 200 | 100 |
| 2 | 200 | 200 | 400 |
| 3 | 200 | 200 | 200 |
| 4 | 400 | 400 | >400 |
| 5 | 200 | 100 | 400 |
| 8 | 100 | 200 | 200 |

Although the present invention has been described in detail with reference to certain preferred versions thereof, other variations are possible. Therefore, the spirit and scope of the appended claims should not be limited to the description of the versions contained therein.

What is claimed is:

1. A method comprising treating a microbe or a habitat of the microbe by administering an effective amount of a compound and allowing the compound to act on the microbe or its habitat, wherein the compound is of formula (I):

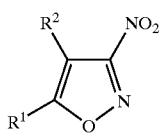

(I)

wherein $R^1$ and $R^2$ independently of one another each represent hydrogen, halogen, nitro cyano, or represent in each case an optionally substituted alkyl, alkenyl, alkynyl or aryl.

2. The method according to claim 1, wherein in formula (I), $R^1$ and R2 independently of one another each represent hydrogen, halogen, cyano, nitro, or represent in each case straight-chain or branched $C_1$–$C_8$-alkyl, $C_2$–$C_8$-alkenyl or $C_2$–$C_8$-alkynyl, each of which is optionally mono- or polysubstituted by identical or different substituents selected from the group consisting of halogens, nitros, cyanos, aryls, aryloxy groups, or $C_1$–$C_6$-alkoxy groups, each substituent which is optionally mono- to nonasubstituted by identical or different halogens, $C_1$–$C_6$-alkylthio, which is optionally mono- to nonasubstituted by identical or different halogens, $C_1$–$C_6$-acyl, $C_1$–$C_6$-acyloxy, $C_1$–$C_6$-alkoxy-carbonyl, amino, which is optionally mono- or disubstituted by identical or different substituents from the group consisting of $C_1$–$C_4$-alkyl and aryl, or represent $C_6$–$C_{10}$-aryl, which is optionally mono- or polysubstituted by identical or different substituents from the group consisting of halogen, cyano, nitro, $C_1$–$C_5$-alkyl, which is optionally mono- to hexasubstituted by identical or different halogens, $C_1$–$C_5$-alkoxy, which is optionally mono- to hexasubstituted by identical or different halogens, $C_1$–$C_5$-alkylthio, which is optionally mono- to hexasubstituted by identical or different halogens, amino, monoalkylamino having straight-chain or branched $C_1$–$C_6$-alkyl radicals, dialkylamino having identical or different straight-chain or branched $C_1$–$C_6$-alkyl radicals.

3. The method according to claim 1, wherein in formula (I), wherein $R^1$ and $R^2$ independently of one another each represent hydrogen, fluorine, chlorine, bromine, cyano, nitro, or represent in each case straight-chain or branched C1–$C_6$-alkyl, $C_2$–$C_6$-alkenyl or $C_2$–$C_6$-alkynyl, each of which is optionally mono- to tetrasubstituted by identical or different substituents from the group consisting of fluorine, chlorine, bromine, nitro, cyano, phenyl, naphthyl, phenyloxy, naphthyloxy, $C_1$–$C_4$-alkoxy, which is optionally mono- to heptasubstituted by identical or different substituents from the group consisting of fluorine, chlorine, bromine, $C_1$–$C_4$-alkylthio, which is optionally mono- to heptasubstituted by identical or different substituents from the group consisting of fluorine, chlorine and bromine, $C_1$–$C_4$-acyl, $C_1$–$C_4$-alkoxy-carbonyl, amino, which is optionally mono- or disubstituted by identical or different substituents from the group consisting of $C_1$–$C_4$-alkyl, phenyl and naphthyl, or represent phenyl or naphthyl, each of which is optionally mono- to tetrasubstituted by fluorine, chlorine, bromine, cyano, nitro, $C_1$–$C_4$-alkyl, which is optionally mono- to tetrasubstituted by identical or different substituents from the group consisting of fluorine, chlorine and bromine, $C_1$–$C_4$-alkoxy, which is optionally mono- to tetrasubstituted by identical or different substituents from the group consisting of fluorine, chlorine and bromine, $C_1$–$C_4$-alkylthio, which is optionally mono- to tetrasubstituted by identical or different substituents from the group consisting of fluorine, chlorine and bromine, amino, monoalkylamino having straight-chain or branched $C_1$–$C_4$-alkyl radicals or dialkylamino having identical or different straight-chain or branched $C_1$–$C_4$-alkyl radicals.

4. The method of claim 1, wherein the compound of the formula (I) treats a microbe on an industrial material or plant and protects the industrial material or the plant.

5. The method of claim 1, wherein the compound of the formula (I) treats an industrial material and protects the material against fungi and bacteria.

6. A microbicidal composition comprising:

(A) a compound of the formula (I)

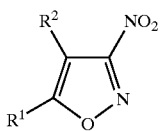

(I)

wherein $R^1$ and $R^2$ independently of one another each represent hydrogen, halogen, nitro, cyano, or represent in each case an optionally substituted alkyl, alkenyl, alkynyl or aryl, (B) solvents or diluents and, (C) optionally processing auxiliaries, or active compounds, or mixtures thereof.

7. A process for preparing a microbicidal composition comprising:

(A) a compound of the formula (I)

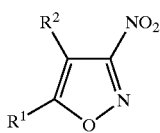

(I)

wherein $R^1$ and $R^2$ independently of one another each represent hydrogen, halogen, nitro, cyano, or represent in each case an optionally substituted alkyl, alkenyl, alkynyl or aryl, (B) solvents or diluents and, (C) optionally processing auxiliaries, or active compounds, or mixtures thereof, the process comprising mixing (i) a compound of the formula (I)

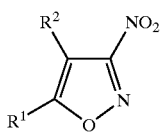

(I)

wherein $R^1$ and $R^2$ independently of one another each represent hydrogen, halogen, nitro cyano, or represent in each case an optionally substituted alkyl, alkenyl, alkynyl or aryl, with (ii) solvents or (iii) diluents and, optionally (iii) with processing auxiliaries, active compounds, or mixtures thereof.

* * * * *